US006623472B1

United States Patent
Reincke et al.

(10) Patent No.: US 6,623,472 B1
(45) Date of Patent: Sep. 23, 2003

(54) METHOD FOR INDUCING THERAPEUTICALLY-EFFECTIVE PROTEINS

(75) Inventors: Julio Reincke, Köln (DE); Hans Meijer, Köln (DE); Peter Wehling, Düsseldorf (DE)

(73) Assignee: Orthogen Gentechnologic. GmbH, Dusseldorf (DE)

( * ) Notice: Subject to any disclaimer, the term of this patent is extended or adjusted under 35 U.S.C. 154(b) by 0 days.

(21) Appl. No.: 09/485,836

(22) PCT Filed: Aug. 5, 1998

(86) PCT No.: PCT/EP98/04866

§ 371 (c)(1),
(2), (4) Date: Jul. 6, 2000

(87) PCT Pub. No.: WO99/09051

PCT Pub. Date: Feb. 25, 1999

(30) Foreign Application Priority Data

Aug. 16, 1997 (DE) .......................... 197 35 537
May 20, 1998 (EP) ............................ 98109186

(51) Int. Cl.⁷ ...................... A61M 31/00; A61M 37/00; A61K 45/00
(52) U.S. Cl. ...................... 604/522; 604/506; 604/4.01; 424/85.2
(58) Field of Search ............................... 604/506, 507, 604/511, 512, 522, 181–182, 187, 199, 200–201, 205, 218, 244, 256, 263, 264, 403, 416, 4.01, 6.15, 6.16; 424/85.2, 130.1, 134.1

(56) References Cited

U.S. PATENT DOCUMENTS 4,118,315 A * 10/1978 Fletcher et al. ......... 210/321.69

FOREIGN PATENT DOCUMENTS

AU  WO89/10974  * 11/1989
EP  88971 A     9/1983

OTHER PUBLICATIONS

W. P. Arend et al: IgG Induction of . . . Immunological Reviews.

V. Ruiz de Souza et al: Selective Induction . . . European Journal of Immunology.

Chemical Abstracts, vol. 125 L.S. Andersen et al: IgG for Intravenous . . . .

* cited by examiner

Primary Examiner—Brian L. Casler
Assistant Examiner—Catherine Serke
(74) Attorney, Agent, or Firm—Randall B. Bateman

(57) ABSTRACT

A method for inducing therapeutically-effective protein includes selecting a syringe having inner structures coated with an inductor, disposing a therapeutically-effective protein therein with a body fluid and incubating the syringe and its contents. The inductor can be coated onto the interior of the syringe itself or can be placed on other structures and inserted into the interior of the syringe. A variety of inductors and body fluids may be used. Anticoagulants may also be used.

25 Claims, 1 Drawing Sheet

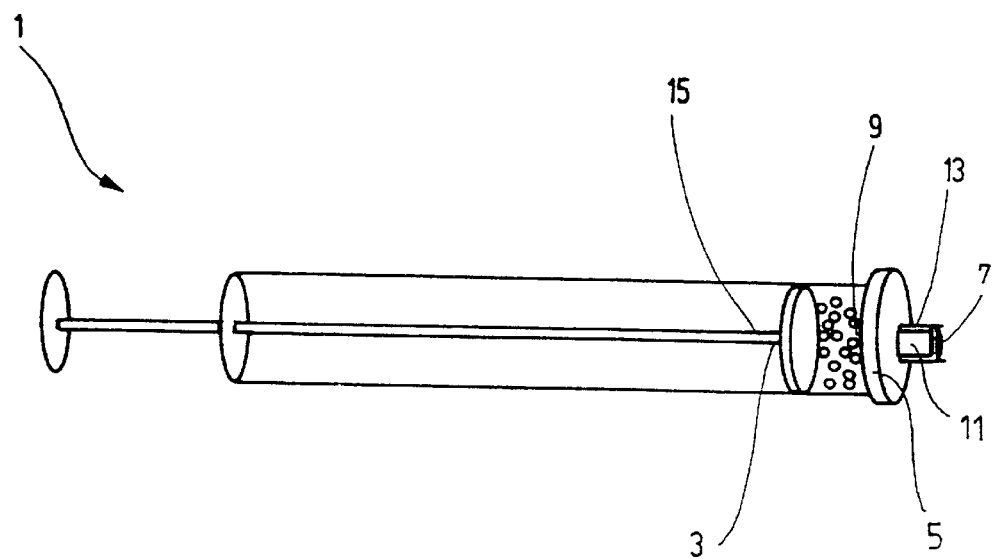
Fig.

METHOD FOR INDUCING THERAPEUTICALLY-EFFECTIVE PROTEINS

The present application is the U.S. National phase of PCT Application PCT/EP98/04866, which claims priority to European Patent Application No. 98109186.1, filed May 20, 1998, and German Patent Application No. 19735537.4, filed Aug. 16, 1997.

This invention relates to a method for producing therapeutically-effective proteins as well as the means used therein, in particular syringes.

Therapeutically-effective proteins, such as erythropoietin, insulin or interferon, have been known for a long time. Many of these proteins are already registered drugs and accordingly are commonly used. Because of the high cost connected with the development and registration of these medications, there is however a need for simple and inexpensive alternatives for the preparation of therapeutically-effective proteins. In addition, not all therapeutically-effective proteins are registered drugs. However, there nevertheless frequently is the requirement to administer these proteins as well as patients. Of particular importance in this context are autologous, that is intrinsic, body proteins because of their presumed good bodily tolerance. Among these proteins are interleukin 1 receptor antagonist, interleukin-4, interleukin-10 and tumour necrosis factor receptor Type I or Type II.

The stimulation of monocytes by adherent immunoglobulin G for the formation of interleukin 1 receptor antagonists is described by Arend and Leung in Immunological Reviews (1994) 139, 71–78 and Moore et al. in Am. J. Respir. Cell Mol. Biol. (1992) 6, 569–575. Andersen et al., in Autoimmunity (1995) 22, 127–33, explained that the therapeutic effect of immunoglobulin G to be observed in vivo cannot be put down to an intensified formation of interleukin 1 receptor antagonist, and that the in vitro formation of interleukin 1 receptor antagonist (IRAP, IL-Ira) occurs by means of monocytes in dependence on serum and plasma components absorbed in polypropylene. Methods of producing IL-Ira directly usable in therapy are not described in these publications.

The underlying technical problem of this invention therefore consists in providing a method and means for preparing therapeutically-effective proteins which serve as inexpensive and rapidly implemented alternatives to the use and preparation of conventional drug preparations.

The invention solves this problem by providing a method for preparing at least one therapeutically-effective protein or a protein mixture in a syringe, in which the inner structures of the syringe are coated with inductors, in particular immunoglobulins, the syringe is filled with a body fluid of a patient, incubated and the therapeutically-effective protein is formed in the body fluid. The invention therefore provides in a first procedure step that the inner structures of the syringe are coated with inductors, in particular immunoglobulins, and these are fixed there. After coating, the syringe is filled in a second procedure step with a body fluid, in particular blood, lymph fluid, saliva or turine, and incubated. Preferably the body fluid is taken with the syringe directly from the patient. The inductors fixed to the inner structure of the syringe, in particular immunoglobulins, induce specifically in the body fluid, i.e. depending on the inductor used, in particular immunoglobulin, and the body fluid used, the formation of therapeutically-effective proteins which are accordingly accumulated, or that is to say formed in the body fluid in the syringe. The body fluid accumulated in this way can be stored in sterile conditions in the syringe and resupplied as or when required to the patient directly without additional treatment or for example after centrifuging and/or sterile filtration.

The invention also provides that the formation of several proteins is induced simultaneously in a body fluid, so that a body fluid is formed which has a raised concentration of several proteins.

In the context of this invention, an inner structure of a syringe is taken to mean any area or any structure of the syringe, which inner structure is inside the syringe and which comes into contact with the body fluid to be contained and which can be coated with inductors, in particular immunoglobulins. Particularly advantageous is the inner structure of a syringe whose inner surface optionally is a surface with a structure for expanding the surface area. The inner structure can however be formed either alternatively or additionally by particles, spheres, gels, glass wool, granulated material or similar, in order to make available a greater surface area for the inductors, in particular immunoglobulins.

In a particular advantageous design of the invention, provision is made for the syringe, in particular the inner structure of the syringe, to be made of polystyrene, polypropylene, glass or a similar material, i.e. consists of these materials or essentially contains these materials, so long as this material processes inductor-binding, in particular immunoglobulin-binding, properties, that is to say adhesion of the inductors, in particular immunoglobulins, is possible. A preferred form of implementation of the invention provides for the production of the inner structure of the syringe, while the inherently non-protein-binding inner structure of the syringe is provided with a protein-binding coating.

This invention is advantageous inasmuch as that an easily implemented method is provided, by which autologous therapeutically-effective proteins, capable of preparation by induction, in particular immunoglobulin induction, can be prepared and in the form prepared this way, i.e. together with the other components of the body fluids in the syringe, can be administered directly to the patient, i.e. without further manipulation such as transfer to another container, for example. If necessary, centrifuging and/or sterile filtration can be provided for separating solid components. The use of commercially available and often expensive drugs is therefore unnecessary. Furthermore, the use of therapeutically-effective autologous proteins is possible which until now have not been legally authorized drugs and therefore not legally available. Finally the invention, which is based on the drug preparation taking place outside the patient, proves to be advantageous in that contamination, impurities, infection or similar of the therapeutically-effective proteins, are avoided.

In a particularly preferred form of implementing this invention, the therapeutically-effective protein is interleukin 4, interleukin 10 or soluble tumour necrosis factor receptor Type I or Type II, especially preferred being interleukin 1 receptor antagonist (or IL-Ira).

In another especially preferred form of implementing this invention, immunoglobulin G is the immunoglobulin with which the inner structure of the syringe is coated. In the context of this invention, immunoglobulin G is understood to mean isolated immunoglobulin G but also immunocomplexes containing immunoglobulin G, preparations containing immunoglobulin G such as sera, plasma or immunoglobulin G Fc fragment, or preparations or complexes containing the latter.

This invention therefore provides, in a particularly preferred form of implementation, for a method of preparing interleukin 1 receptor antagonists, whereby the inner structure of a syringe is coated with an inductor, in particular an immunoglobulin, and especially preferred immunoglobulin G, the syringe is filled with a body fluid, preferably blood, is incubated and the interleukin 1 receptor antagonist is formed and accumulated in the body fluid. Through the binding or adhesion of the inductor, in particular immunoglobulin G, on the surface of the inner structure of the syringe, the latter is in a position to stimulate the monocytes in the blood to form interleukin 1 receptor antagonist, so that this is accumulated in the blood. After incubation, i.e. after accumulation of the interleukin 1 receptor antagonist, the blood in the syringe can be supplied without further manipulation, such as transferring into another container for example, directly to the patient from whom the blood put into the syringe had been taken. For separation of solid components, such as cells, centrifuging and/or sterilization can be advantageously provided. The invention therefore also provides that the blood can be taken from the patient by means of the inductor-coated, in particular immunoglobulin G-coated, syringe, the blood can be incubated in the syringe and, after IL-ira information, can be supplied to the patient again with the syringe. Such a procedure is, for example, especially advantageous in the field of neuro-orthopaedics, i.e. for example in the case of neurologically-caused back complaints. Hitherto only an intervertebral disc operation, cortisone treatments, irrigation procedures using saline solutions or similar, were considered for the treatment of this type of complaint. This invention now allows the simple and inexpensive provision of a therapeutically-effective protein for treating these complaints.

In another preferred form of implementations, the invention provides that the inner structure of the syringe is coated additionally with anticoagulants, in particular heparin. According to the invention, the anticoagulation can also be provided not as a coating but to be introduced uncombined in the container, for example to be put into the syringe in the dry frozen or liquefied state.

In another preferred form of implementation, the invention provides for the incubation of the body fluid in the syringe over a period of 12 to 72 hours, preferably carried out at an ambient temperature up to 41° C., in particular 37° C.

In one form of the invention, the invention also provides that after the formation of the therapeutically-effective protein in the body fluid, the body fluid is further processed in order to separate for example certain components of the latter, for example blood plasma or blood platelets. This separation process can be performed, in a preferred form of implementation of the invention, by centrifuging.

In a further form of implementation, the invention concerns a method of producing a syringe, suitable for in vitro induction of interleukin 1 receptor antagonists, in which an inductor, preferably an immunoglobulin, in particular immunoglobulin G, is placed in the syringe with a protein-binding inner structure and incubated so that the inductor, in particular the immunoglobulin G, binds to the inner structure.

It is self-evident that the invention also concerns the syringe produced in this way, which is manufactured in a particularly preferred form of implementation from polystyrene, polypropylene or glass, the syringe being distinguished by a coating of its inner structure with an inductor, in particular with an immunoglobulin, preferably with immunoglobulin G.

The invention also relates to the use of immunoglobulin, in particular immunoglobulin G, for coating the inner structures of syringes, preferably made of polystyrene, polypropylene or glass, for the in-vitro induction of therapeutically-effective proteins, preferably interleukin 1 receptor antagonists.

Additional advantageous forms of the invention emerge from the sub-claims.

The invention is explained in more detail with reference to figures and examples of implementation.

BRIEF DESCRIPTION OF THE DRAWINGS

The FIGURE shows in schematic representation a syringe according to the invention.

DETAILED DESCRIPTION

Example 1

The FIGURE shows a syringe 1 made of polystyrene with a piston 3, a sealing cap 5 (which can be unscrewed) with a cap extension 13 (male Leur [sic]) and a removable cap 7 with a septum arranged on, and blanking off, the cap extension 13. The piston 3 has a predetermined breaking point 15. Also shown is granulated material 9 made of polystyrene coated with IgG (not represented). The size of the granulated particles 9 is between 1 and 3 mm diameter, though smaller particles, in particular larger than 100 $\mu$m also can be used.

To prepare the syringe 1, the granulated material 9 is coated with a commercially available IgG preparation (Venimmune®, Behring), while the IgG preparation is taken into the syringe and the granulated material as well as the syringe inner wall is moistened by the IgG preparation. Then the syringe 1 is incubated at ambient temperature for at least 15 minutes, in order to ensure a complete bond with the granulated material 9 and the syringe inner wall. Finally heparin (liquemin N 2500, heparin solution 2500 I.E.) or citrate (ACDA) is put into the syringe so as to prevent coagulation of the blood to be taken in later.

The syringe 1 is used, while blood of patient is taken with the aid of an adapter (not shown), which connects the removable cap 7 with a cannula (not shown) by means of a flexible tube (not shown). The adapter has a needle, by means of which the septum in the cap extension 13 is pierced. Then the adapter is removed and incubation of the complete blood carried out at 37° C. for 24 hours protected by the removable cap 7, whose septum has automatically sealed itself. Incubation can occur in a vertical or horizontal position. If incubation is carried out in the vertical position, the plasma is removed through the septum and a sterile filter attachment (0.2 $\mu$m). Additionally or alternately, a centrifuging process can be provided. If incubation is carried out in the horizontal position, the blood is centrifuged and the plasma removed through a sterile filter attachment (0.2 $\mu$m). However, provision can be made for the plasma to be removed through the septum without carrying out centrifuging. The plasma is then reinjected, for example, in a nerve ending or joint of the patient.

Example 2

Syringe With Granulated Material

Sterile granulated material made of polystyrene, glass or another non-pyrogenic protein-binding material is coated with protein (for example an IgG preparation registered under AMG (e.g. Venimmun®, Behring) under sterile conditions in a batch process in sterile water or aqueous buffer diluted to 10 to 100 $\mu$m/ml) and then dried.

A conventional polypropylene syringe (5, 10, 20 or 50 ml) is filled with the protein-coated granulated material (1, 2, 4 or 10 cm²) as well as with a sufficient quantity of an anticoagulant such as heparin (liquemin, heparin sodium 2500 I.E.) or citrate (for example ACDA).

The filled syringe is packaged including receiving cannula and flexible tube and then sterilised by gamma radiation or electron [sic] radiation. This ensures a pyrogen-free product.

The user removes the sterile instrument set and takes blood from the patient. At its opening in the cap extension above, the syringe has a septum which is pierced by the receiving attachments, that is the needle of the adapter, for the taking of the blood. After removal of the adapter, the septum automatically reseals itself. The syringe piston is broken off at a predetermined breaking point after taking the blood.

The syringe with blood is incubated for 24 hours at 37° C. to 41° C.
 a) If the incubation is carried out in the vertical position, the plasma is removed through the septum and a sterile filter attachment, for example 0.2 μm.
 b) If the incubation is carried out in the horizontal position, the plasma is removed through a sterile filter attachment, for example 0.2 μm after centrifuging the syringe.

Reinjection of the plasma is carried out, for example, at a nerve ending, in the joint or in the intervertebral disc.

Example 3

Syringe Without Granulated Material

A syringe made of a non-pyrogenic protein-binding material (5, 10, 20 or 50 ml) is coated in sterile conditions with protein (for example a commercial IgG preparation registered under AMG (e.g. Venimmun®, Behring)), if necessary in sterile water or aqueous buffer diluted to 10 to 100 μm/ml). Preferably the syringe is made of polystyrene, glass or a specially modified other material.

The coated syringe is filled with a sufficient quantity of heparin (liquemin, heparin sodium 2500 I.E.) or citrate (ACDA).

The coated and filled syringe, including receiving cannula and flexible tube is then sterilised by gamma radiation or electron [sic] radiation. This ensures a pyrogen-free product.

The user removes the sterile instrument set and takes blood from the patient. Contained in the cap extension at the opening above, the syringe has a septum which is pierced by the receiving attachments, that is the needle of the adapter, for the taking of the blood. After removal of the adapter, the septum automatically reseals itself. The syringe piston is broken off at a predetermined breaking point after taking the blood.

The syringe with blood is incubated for 24 hours at 37° C. to 41° C.
 a) If the incubation is carried out in the vertical position, for example in a test tube stand, the plasma is removed through the septum and filtration carried out through a sterile filter attachment, for example 0.2 μm.
 b) If the incubation is carried out in the horizontal position, after centrifuging the syringe the plasma is removed through the septum, in the process a filtration being carried out through a sterile filter attachment, for example 0.2 μm.

Reinjection of the plasma is carried out, for example, at a nerve ending, in the joint or in the intervertebral disc.

Example 4

Preparation of Interleukin 1 Receptor Antagonists in a Syringe Using Heparin

A commercially available and legally authorised drug immunoglobulin G preparation (Venimmun®, Behring) is diluted in a sterile aqueous buffer to 10 to 100 μg/ml.

This solution is filled into a sterile syringe mode of polystyrene, whose inner surface effectively binds protein. Then an incubation of at least 15 minutes is carried out at ambient temperature to saturate the inner wall surface with the immunoglobulin G. The incubation period can also be more than 24 hours.

After completing the incubation, and therefore after adhesion of the immunoglobulin G in the inner surface of the syringe, the immunoglobulin G solution is removed from the syringe and the syringe is temporarily stored in sterile conditions. A legally authorised drug heparin (liquemin, heparin sodium 2500 I.E.), acting as an anticoagulant, is drawn up into the coated syringe.

Using the coated syringe, venous blood is subsequently taken from the patient in sterile conditions.

The syringe is incubated at ambient temperature for 12 to 72 hours. In this time a large accumulation of the proteins, in particular the interleukin 1 receptor antagonists, contained in the plasma, occurs in the blood plasma. A concentration of 1 to 50 mg/ml of the interleukin 1 receptor antagonists could be determined.

Then, using the coated syringe, the blood or the plasma is injected into the patient.

Example 5

Preparation of the Interleukin 1 Receptor Antagonists in a Syringe

A commercially available and legally authorised drug immunoglobulin G preparation (Venimmun®, Behring) is diluted in a sterile aqueous buffer to 10 to 100 μg/ml.

This solution is filled into a sterile syringe made of polystyrene, whose wall material effectively binds protein. Incubation is carried out at ambient temperature over at least 15 minutes, which serves to saturate the inner wall surface with the immunoglobulin G.

After completing the incubation and adhesion of the immunoglobulin G to the inner surface of the syringe, the immunoglobulin G solution is removed and the syringe is temporarily stored in sterile conditions.

Using the coated syringe, venous blood is subsequently taken from the patient in sterile conditions.

The syringe is incubated at ambient temperature for 12 to 24 hours. In this time a large accumulation of the proteins, in particular the interleukin 1 receptor antagonists, contained in the plasma, occurs in the blood plasma. A concentration of 1 to 50 mg/ml of the interleukin 1 receptor antagonists could be determined.

Then using the coated syringe, the blood or the plasma is injected into the patient.

What is claimed is:

1. A method for preparing at least one therapeutically-effective protein in a syringe, the method comprising:
 placing an inductor and a therapeutically-effective protein inside a syringe;
 filling the syringe with a body fluid;
 incubating the syringe until additional therapeutically-effective protein is formed in the body fluid.

2. The method according to claim 1, in which the inductor is an immunoglobulin.

3. The method according to claim 2, wherein the immunoglobulin is immunoglobulin G (IgG).

4. The method according to claim 1, in which the therapeutically-effective protein is selected from the group consisting of interleukin 1 receptor antagonist (IRAP), interleukin 4, interleukin 10 and soluble tumour necrosis factor receptor Type I or Type II.

5. The method according to claim 1, wherein the method comprises coating inner structures of the syringe with an inductor.

6. The method of claim 1, wherein the method comprised disposing an inductor on at least one of the group consisting of spheres, gels, glass wool, granulated material and particles in the syringe.

7. The method according to claim 1, wherein the inductor is disposed on one of the group consisting of materials polystyrene and glass disposed in the syringe.

8. The method according to claim 1, wherein the method further comprises disposing anticoagulants in the syringe prior to incubation.

9. The method according to claim 1, wherein the body fluid is blood.

10. The method according to claim 1, wherein the method comprises incubating the syringe between 12 and 72 hours.

11. The method according to claim 1, wherein the inductor comprises immunoglobulin, and the therapeutically-effective protein is selected from the group consisting of interleukin 1 receptor antagonist (IRAP), interleukin 4, interleukin 10 and soluble tumour necrosis factor receptor Type I or Type II.

12. The method according to claim 11, wherein the method further comprises disposing anticoagulants in the syringe.

13. The method according to claim 1, wherein the therapeutically-effective protein is contained in the body fluid when the body fluid is placed in the syringe.

14. A method for preparing a syringe suitable for in vitro induction of therapeutically-effective proteins, comprising:

placing inductors in a syringe with protein-binding inner structures, the inductors comprising immunoglobulin IgG; and incubating the syringe so that the inductors bind to the inner structures.

15. The method according to claim 14, wherein the inner structures of the syringe comprise at least one of the group consisting of materials comprising polystyrene and material comprising glass.

16. The method according to claim 15, wherein the inner side of the syringe is coated with the inductor.

17. The method according to claim 15, wherein the inductor is disposed on at least one of the group consisting of spheres, gels, glass wool, granulated material and particles disposed in the syringe.

18. A method according to claim 14, wherein the therapeutically-effective protein is IRAP.

19. A method for preparing at least one therapeutically-effective protein in a syringe, the method comprising:

placing an inductor inside a syringe;

filling the syringe with a body fluid; and incubating the syringe until a desired therapeutically-effective protein is formed in the body fluid during incubation.

20. The method according to claim 19, in which the inductor is an immunoglobulin.

21. The method according to claim 20, wherein the immunoglobulin is immunoglobulin G (IgG).

22. The method according to claim 19, in which the therapeutically-effective protein is selected from the group consisting of interleukin 1 receptor antagonist (IRAP), interleukin 4, interleukin 10 and soluble tumour necrosis factor receptor Type I or Type II.

23. The method according to claim 19, wherein the method comprises selecting a body fluid having a therapeutically-effective protein and forming additional amounts of the therapeutically effective protein in the body fluid during incubation.

24. The method according to claim 19, wherein the method comprises placing an inductor on at least one of the group consisting of spheres, gels, glass wool, granulated material and particles in the syringe.

25. The method according to claim 19, wherein the method comprises selecting a body fluid not having the therapeutically-effective protein and using the inductor to form the therapeutically-effective protein in the body fluid.

* * * * *

UNITED STATES PATENT AND TRADEMARK OFFICE
CERTIFICATE OF CORRECTION

| | | |
|---|---|---|
| PATENT NO. | : 6,623,472 B1 | Page 1 of 1 |
| APPLICATION NO. | : 09/485836 | |
| DATED | : September 23, 2003 | |
| INVENTOR(S) | : Julio Reincke, Hans Meijer and Peter Wehling | |

It is certified that error appears in the above-identified patent and that said Letters Patent is hereby corrected as shown below:

On the Title Page:

Item [73] Assignee: replace "Orthogen Gentechnologic. GmbH" with
-- Orthogen Gentechnologie GmbH --

Signed and Sealed this

Thirty-first Day of July, 2012

David J. Kappos
*Director of the United States Patent and Trademark Office*